United States Patent [19]

Scrivener et al.

[11] Patent Number: 4,502,327
[45] Date of Patent: Mar. 5, 1985

[54] ROAD TESTING APPARATUS

[75] Inventors: Stephen P. Scrivener, Glenbrook; Wallace D. Smith, Willoughby; Mark L. Mansell, Gymea; Neville D. Campbell, Dundas, all of Australia

[73] Assignee: The Commissioner for Main Roads, Sydney, Australia

[21] Appl. No.: 491,649

[22] Filed: May 5, 1983

[30] Foreign Application Priority Data

May 6, 1982 [AU] Australia .................. PF3888

[51] Int. Cl.³ .................................... G01N 19/00
[52] U.S. Cl. ....................................... 73/146
[58] Field of Search .................... 73/146, 7, 9, 104

[56] References Cited

U.S. PATENT DOCUMENTS

| 2,290,618 | 7/1942 | Bosomworth | 73/146 |
| 3,332,276 | 7/1967 | Clarke | 73/146 |
| 3,444,727 | 5/1969 | Bourdin et al. | 73/146 |

FOREIGN PATENT DOCUMENTS 2148362 11/1972 Fed. Rep. of Germany .
2742110  3/1979 Fed. Rep. of Germany .
1283460  7/1972 United Kingdom .

OTHER PUBLICATIONS

"An Investigation of a Full-Scale Flexible Pavement Subjected to Simulated Traffic Loading"—B. Shackel and M. G. Arora, 1978.

"The Design of a Model Test Track"—H. Taylor, 1966.
"The Heavy Vehicle Simulator System in South Africa", B. Shackel, 1980.

Primary Examiner—Donald O. Woodiel
Attorney, Agent, or Firm—David W. Selesnick

[57] ABSTRACT

A road testing apparatus has a framework extending over a test portion of road pavement and has tracks with upwardly curved ends along which wheels of a trolley unit roll so that the trolley unit decelerates as it approaches an end position to cause kinetic energy to be transformed into potential energy and when return motion trolley commences the potential energy transforms back to kinetic energy. The trolley unit has a pivotally mounted base structure carrying a test load and a pair of road wheels which are mounted so as to be steered by the trolley as it progresses in a forward direction along the test pavement, additional wheels of the trolley running up an end portion of the track to lift the road wheels off the road surface as the end position is reached. A telescopic linkage latches into engagement at this end position to retain the road wheels in an elevated position relative to the trolley so that, during return motion, the road wheels can continue to rotate in the same direction but engage on the bottom of a base plate structure of the framework to drive the trolley in the reverse direction, the latch arrangement being released when the trolley reaches the opposite end position to permit a further cycle of operations.

20 Claims, 8 Drawing Figures

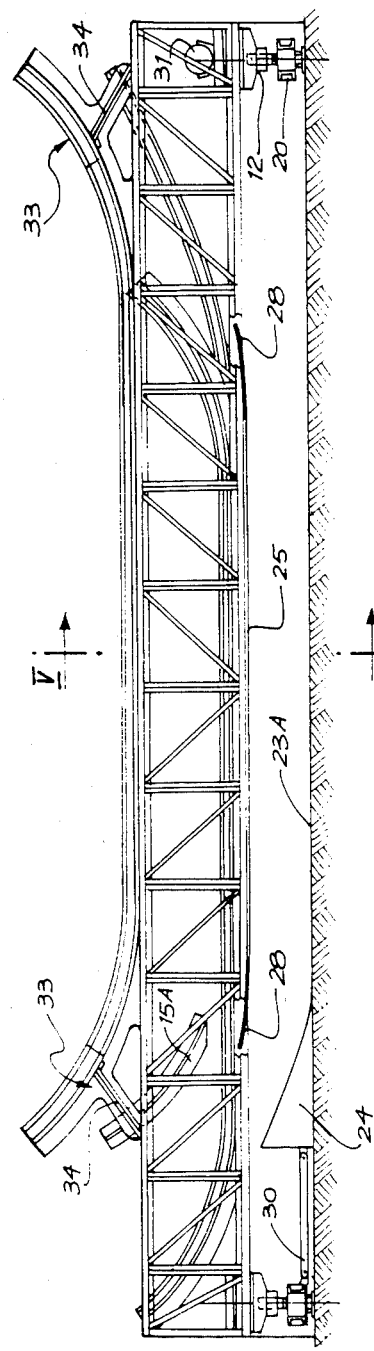
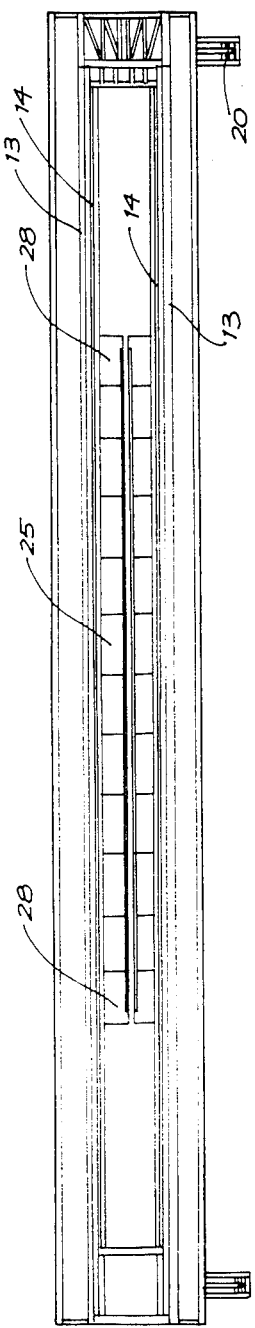
FIG. 2
FIG. 3

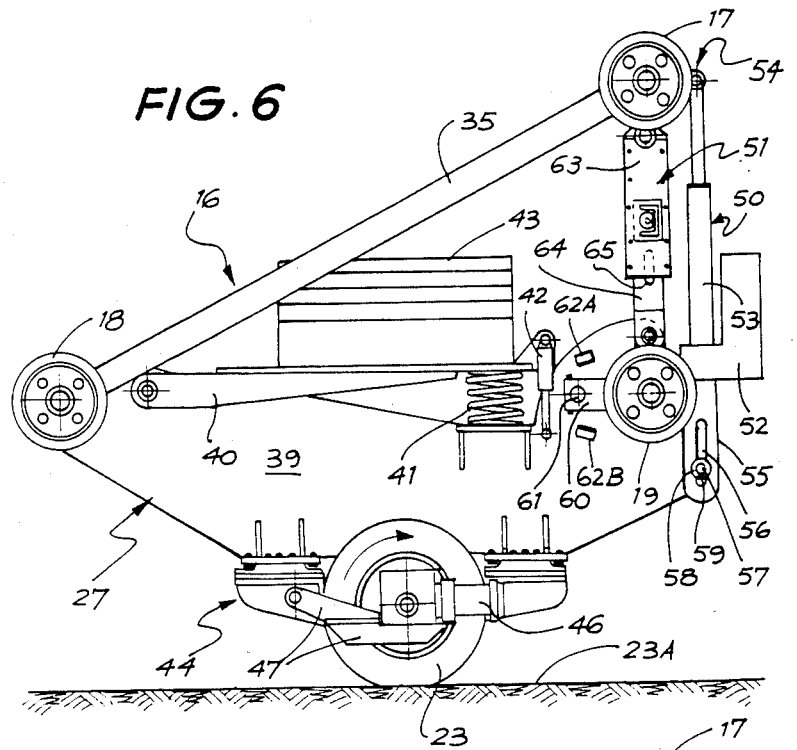
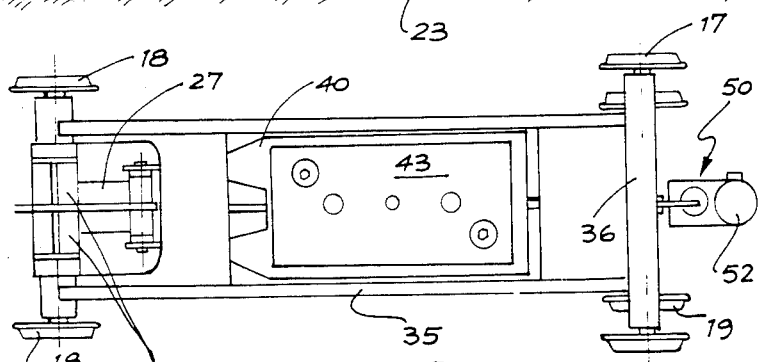

ROAD TESTING APPARATUS

The present invention relates to an apparatus for testing road pavements.

Road construction is an extremely expensive undertaking and is complex in that failure and breakdown of a road pavement can be due to a large number of factors including local conditions, types of materials used, the nature of the traffic using the road and many other variables. The high cost of roads is such that an accelerated testing arrangement is needed to evaluate road pavement materials, pavement designs and construction techniques.

Several proposals for testing roads have been based on the use of circular or oval test tracks with loaded road wheels mounted on a movable structure and continuously run around the track in order to provide repeated loadings of the test pavement. Proposals for such systems have been very expensive but also have the disadvantage of requiring specially constructed circular test pavements, and thus there can be no tests on actual roads constructed at various locations. It may be impracticable to create an accurate reproduction of an actual load at a remote test facility.

Other proposals include a linear test track for laboratory scale operations in which the test wheel is scaled down, the wheel being run back and forth along the test track. Such an arrangement has been described by H. Taylor in the proceedings of the Third Australian Road Research Board Conference (3) (2.pp1092-1099).

Disadvantages associated with such scaling down have been discerned. There is a need for a full scale accelerated loading arrangement for testing actual road pavements as well as specially constructed test sections.

Another proposal described in SHAKEL B. & ARORA M. G. (1978) "The Application of a Full Scale Road Simulator to the Study of Highway Pavements", Australian Road Research 8(2) pp. 17-31, is a repetitive loading simulator comprising a concrete trough in which a small section of the pavement to be tested is built; a series of powerful hydraulic rams are mounted on a gantry to load sequentially the pavement to simulate a loaded wheel moving along the pavement at low speed. It is considered that the adequacy of this simulation is very doubtful.

On-site testing of actual road pavements has been done in South Africa with a "Heavy Vehicle Simulator". This apparatus is an expensive vehicle-like device which internally mounts, in a complex way, a test wheel which is hydraulically loaded and towed back and forth over a few meters of road. This apparatus requires considerable operating power and is very noisy.

The present invention is based upon the concept of a transportable rig for on-site testing of actual road pavements in a realistic manner but with economy and in a manner which effectively simulates long term traffic usage in a short period of time.

The present invention provides apparatus for testing a test portion of road pavement extending between first and second positions, the apparatus comprising:

(a) a support for carrying a test load, (b) a hub for rotatably mounting a road wheel on the support.

(c) mounting means for displaceably mounting and guiding the support for displacement generally between said first and second positions, (d) means for moving the support forwardly from the first position to the second position with the road wheel rolling along the test portion, and means for returning the support from the second position to the first position with the road wheel held out of contact with the test portion, (e) height control means for lifting the hub to hold the road wheel out of contact with the road surface at the region of the second position, and for lowering the road wheel onto the test portion during commencement of motion of the support from the first position towards the second position, and (f) energy conversion means for decelerating the support and test load as it approaches the first and second positions and converting the kinetic energy thereof into potential energy and then using the potential energy to accelerate the support and test load in the opposite direction.

Very importantly the invention provides an apparatus which can be energy efficient, very economically manufactured, transportable from site to site, and highly effective in its simulation of traffic since the road wheel can continuously rotate in a single direction and the road is "rolled" only in one direction.

The present invention may be embodied in various forms and various optional features described below may be included as desired.

In a preferred embodiment of the invention, the apparatus is dimensioned and constructed to carry full scale test loads on a full size road pavement. Usually it will be desirable to design a road pavement to have a useful working life when carrying heavily laden trucks and an accepted test requirement is for the pavement to withstand a specified number of passes of a wheel loaded to at least the maximum permissible weight according to road regulations. In the context of Australian road building, it is considered that a static load of 40 kN (being the legal limit) is an appropriate test load for accelerated testing, and the invention is preferably embodied in an apparatus which can achieve one million passes in a period of the order of 100 days. However, it is desirable to construct the apparatus so that a static load of between 40 kN and 100 kN can be applied for special testing purposes.

In an important embodiment of the invention, the mounting means comprises an elongated track, the support has wheel means arranged to run along the track, and the energy conversion means includes upwardly extending end portions for the elongated track.

Preferably, the height control means comprises means to utilise kinetic energy of the decelerating support and test load as they approach the second position to lift the hub and has latching means to hold the hub in an elevated position. This is an important and advantageous feature, since effective energy use lowers substantially power requirements with large cost savings in equipment.

In an highly advantageous and important embodiment of the invention the elongated track includes first and second track portions, the wheel means of the support includes first and second wheel means rotatably mounted on an upper structure of the support for engagement respectively on the first and second track portions and having axes on opposite sides of said hub, the hub being mounted on a base element pivotally mounted to the upper structure in the region of the second wheel means, and the height control means comprises:

(i) third wheel means rotatably mounted on said support at a location generally vertically spaced relative to the first wheel means (ii) a third track portion parallel to and offset laterally relative to said first and second track portions and with end portions which become closer to the first track portion on approaching either end of said track portions, and (iii) holding means including:
 (a) a linkage extending upwardly between and connected to the upper structure and the base element at locations on the opposite side of a vertical through the hub compared to the second wheel means, and
 (b) selectively operable fixing means for fixing the linkage in a shortened condition when the support reaches said second position whereby the road wheel is arranged to be held out of contact with the test portion during return motion of the support to the first position, at which location the fixing means releases.

Advantageously, the moving means comprises at least one drive motor arranged to drive the road wheel (or pair of road wheels) on the road surface, thereby moving the hub and support from the first position to the second position. With this embodiment it is furthermore preferable to provide in the mounting means an elongated engagement structure against which the road wheel is adapted to engage thereby driving the support and hub in the return direction to the first position, but with the road wheel rotating in the same direction for both forward and return motions.

Another very important feature comprising a further inventive concept which is preferably embodied in the present apparatus, is the provision of means for varying the path taken by the road wheel along the test surface, the variation available being through a relatively small range of positions extending laterally over the road pavement. In a preferred embodiment, this feature is provided by the mounting means being mounted at its respective end portions on carriages adapted to move on wheels laterally on the road surface. Preferably, this is arranged through laterally extending tracks positioned on the road pavement, control means being provided for automatically varying randomly but in a normal distribution the exact line along which the road wheel moves during each pass during a test.

For illustrative purposes only an embodiment of the invention will now be described with reference to the accompanying drawings of which:

FIG. 2 is a side elevation of the embodiment of FIG. 1 but with a trolley structure removed;

FIG. 3 is a plan view of the embodiment of FIG. 2;

FIG. 6 is a side elevation showing the trolley structure in detail when arranged for forward motion with the road wheel engaging the test pavement;

FIG. 8 is a plan view of the trolley structure of FIGS. 6 and 7.

Figure 1:
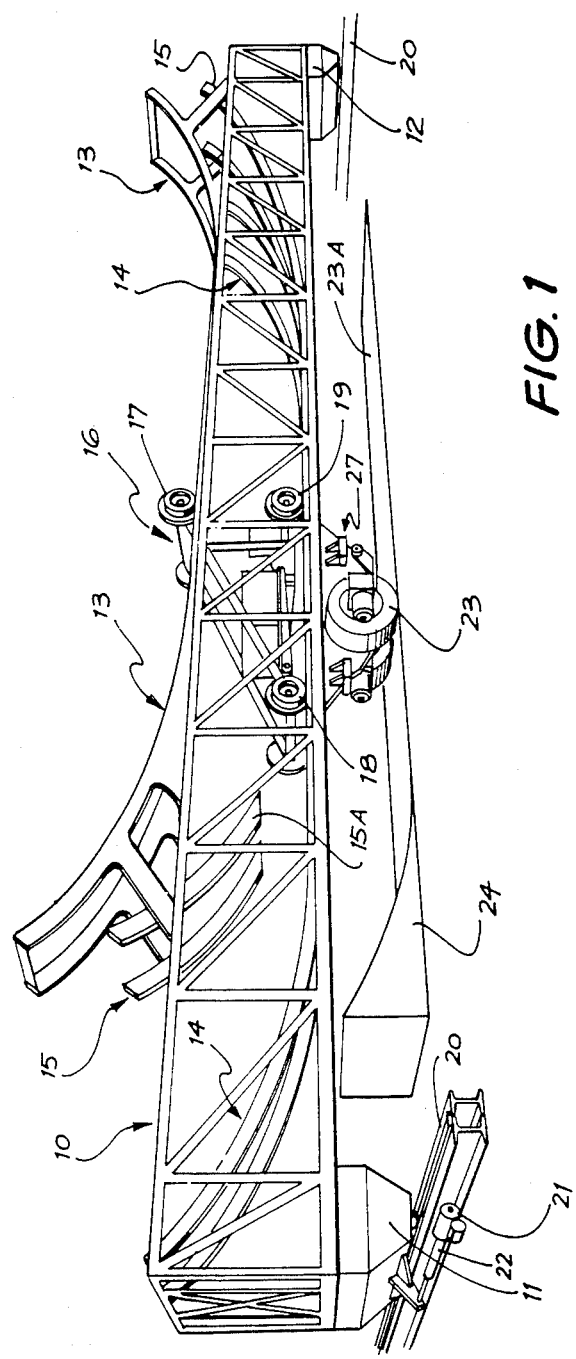
FIG. 1 is a perspective view of an embodiment of the invention.

The apparatus comprises a steel framework 10 of generally rectangular shape extending between a first end carriage 11 and a second end carriage 12 with first, second and third tracks respectively numbered 13, 14 and 15 provided for mounting a rolling trolley structure 16 having first, second and third sets of wheels 17, 18 and 19 running on their respective tracks 13, 14 and 15.

The carriages 11 and 12 are mounted via respective wheels on cross beams 20 having respective rails, lateral displacement being made by electric motors 21 on each cross beam for displacing the frame work by virtue of a screw and nut actuator 22. This displacement is to vary the path of a road wheel across a test strip 23A of a road pavement.

The general principle of operation is that the trolley structure 16 moves to the right with a load carried on a pair of pneumatic road wheels 23 which simulate the load of a truck and when the trolley approaches the right hand end, the road wheels are lifted off the road surface and kinetic energy is translated into potential energy as the wheels of the trolley move up the curved tracks; return acceleration of the trolley converts the potential energy to kinetic energy and the trolley returns to the left hand end of the apparatus with the road wheel held raised above the road surface. Indeed, very importantly the road wheel is driven continuously and drives against the bottom of base plates 25 thereby gradually inputting kinetic energy to compensate for the potential energy acquired by raising the road wheels, the trolley being gradually accelerated to the desired velocity. Thus, capital and operational costs are held down by minimising power requirements.

When the trolley reaches its left hand or first position, the road wheels are permitted to be lowered and to engage upon a fixed inclined ramp 24 as test load is gradually taken up before the road wheels roll onto the test strip 23 for a further pass simulating movement of truck wheels along a road pavement.

Between successive passes the carriages 11 and 12 can be moved laterally to a randomly selected position and in order to provide an effective simulation of road usage, the position of the road wheels is varied in accordance with a normal distribution between limit positions.

Figure 5:
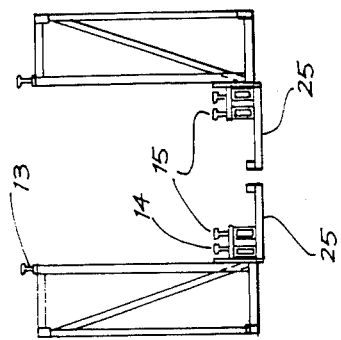
FIG. 5 is a sectional end elevation taken along the line V—V of FIG. 2 and omitting the upwardly extending end portions of the tracks for the purpose of clarity.
Figure 4:
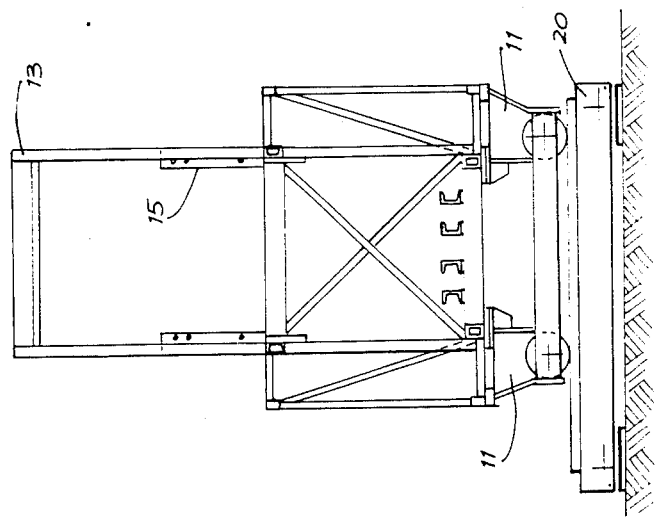
FIG. 4 is an end elevation of the embodiment of FIGS. 2 and 3.

FIGS. 2 to 5 show more detail of the construction and as will be best seen from FIG. 5, each of the first, second and third tracks 13, 14 and 15 are provided by a pair of laterally spaced rails although the third track 15 has a gap at its left hand end as shown in FIG. 1. The braced steel framework 10 carries the flat base plates 25 along the central region of the apparatus with a small gap between the plates as shown in FIG. 5 for accommodating a fin of the base structure 27 of the trolley, the base plates having upwardly curved lead-in end portions 28 shown in the cutaway portions of FIG. 2.

Further detail shown in FIG. 2 includes bracing struts 30 for the inclined ramp 24 and an electric winch 31 at the right hand end for a winch cable for initially moving the trolley to the extreme right hand elevated position as part of a start-up procedure. The trolley is secured with a latch mechanism (not shown), the cable is disconnected and the latch disengaged to release the trolley; relatively low power electric motors 46 (described below) are activated to propel the trolley back to the left hand or first end.

FIG. 2 also shows detachable top portions 33 at each end comprising a support structure and the end portions of the first tracks. These top portions 33 are bolted through connection flanges 34 to the main portion of the framework, the purpose of detachability being to reduce the height of the apparatus for safe road transportation from site to site.

It will be also noted that the radius of curvature of the left hand end portion 15A of the third track has a smaller radius of curvature than the other end portions, this radius of curvature being chosen to suit operation of the trolley unit, as described below and the radius of curvature of the right hand end of the third track is greater than that of the first and second track end portions.

Figure 7:
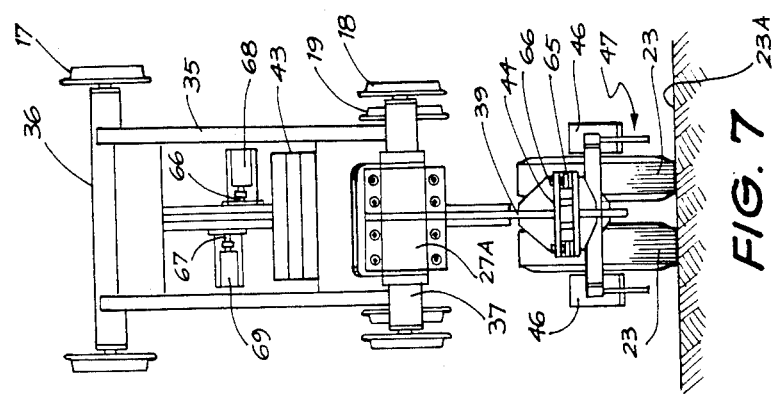
FIG. 7 is an end elevation from the left hand end of FIG. 6.

Referring now to FIGS. 6 to 8, the trolley structure generally indicated by reference 16 comprises an upper rectangular frame including a pair of tubular members 35 mounted between upper and lower cross tubes 36 and 37 which mount axles for the first and second sets of wheels 17 and 18 which are flanged wheels arranged to continuously engage upon the first and second tracks. The trolley also includes a base structure 27 pivotally connected via bolted end shells 27A to the cross tube 37 and having a pivotal platform 40 mounted thereon and supported by a suspension comprising a helical compression spring 41 (which can be replaced by an air bag to simulate an alternative truck suspension) and shock absorbers 42 in order to support a ballast load 43. The base structure 27 also includes a plate-like fin 39 extending downwardly to a hub unit 44 rotatably mounting a pair of road wheels 23 having respective geared electric motors 46 driving directly the road wheels. The electric motors are connected via torque reaction brackets 47 to the hub structure 44.

At the left hand end shown in FIGS. 6 and 8, the trolley includes a static lifting arrangement 50, and a linkage arrangement 51 which co-operates with the third set of wheels 19.

The static lifting arrangement 50 comprises an electric actuator 52 arranged to operate a nut and screw type device 53 which, at its upper end, is connected through a pin connection 54 to the cross tube 36 and at the lower end has a lifting bracket 55 with an elongated slot 56 for accommodating in sliding relationship a bottom pin 57. The bottom pin 57 extends through a circular hole in a nose portion of the fin 39 and passes through a washer 58 to be secured by a split pin 59. Thus, normally the fin 39 can move vertically relative to the lift bracket 55 through a range of positions. However, for example to change tyres it is necessary to lift the base structure 27 so that the tyres are clear of the road test strip 23A and this is simply accomplished with the trolley in a stationary condition by operation of the electric actuator 52. Furthermore, this lifting function is required for certain conventional road testing techniques (such as Benkleman Beam Tests) in which the trolley is positioned laterally as desired before the wheel is lowered and a separate winch (not shown) is used for slow motion longitudinal displacement of the trolley.

The linkage arrangement 51 is normally used during dynamic road testing. The third wheels 19 are mounted on respective pivotal arms 60 which are clamped to respective axles 61, limit stops 62A and 62B being schematically illustrated for limiting displacement of the wheels in the vertical direction.

The linkage arrangement 51 comprises upper and lower telescopically engaging links 63 and 64 which are pivotally connected respectively to the cross tube 36 and the fin 39. The lower link has an elongated slot 65 which receives locking pins when the road wheels are lifted at the end of a forward motion (at the right hand end of the apparatus as shown in FIG. 1). As most clearly shown in FIG. 7, the locking pins comprise first and second locking pins 66 and 67 connected to respective solenoids 68 and 69 and having respective springs (not shown in the drawings) but arranged such that the lower or first pin 66 is spring biased into engagement with the slot 65 when it is presented to the location of the pin upon telescopic contraction of the linkage from the position shown in FIG. 6, but the second pin 67 is spring biased out of engagement, the respective solenoids operating against the spring biasing.

As the trolley unit approaches the right hand end of the apparatus, the road wheels 23 have been carrying the ballast load on the test pavement 23A with the wheels 17 and 18 carrying essentially the load of the upper trolley frame, the third wheels 19 running along the third track just under their own weight and providing a steering function. As the track curves upwardly, the third wheels 19 move with their respective arms 60 to engage the upper stops 62A and the shape of the respective curved tracks causes the weight of the road wheels to be taken on the second and third wheels 18 and 19 and the linkage 51 to be contracted. When the top of the slot 65 reaches the position of the first pin 66 it moves to the left as shown in FIG. 7 to pass through the slot and engage a corresponding circular aperture in the opposite side plate of the upper link 63. The link continues to be contracted and the second pin 67 becomes aligned when an upper portion of the slot 65 while a control device powers the solenoid 69 to positively displace the pin 67 against a spring biasing to engage this slot.

As return motion commences and acquired potential energy is converted into kinetic energy, the linkage expands a little as the third wheels 19 drop relative to the first wheels 17 until the upper pin 67 takes the load and the load is carried by the first and second wheels 17 and 18. Thus, the load is removed from the third wheels 19 which are then engaging the lower stops 62B and are held above the level of the third track. When the trolley unit reaches the horizontal section of the track, the road wheels 23 come into engagement with the base plates 25 and positive drive from the electric motors 46 returns the trolley to the left hand end whereupon the first and second wheels 17 and 18 climb the respective upwardly curved track portions and the road wheels 23 pass the left hand extreme end of the base plates 25 thereby leaving the kinetic energy of the moving trolley assembly to be converted into potential energy as it moves up the tracks. The third wheels 19 then pass over the gap in the third track to engage the end portion 15A which has a smaller radius of curvature, whereby rapidly load is transferred essentially from the first wheels 17 to the third wheels 19 thereby reducing the load carried through the second pin 67. The apparatus is provided with a control device (not shown) so that before the limit position is reached at the left hand end, the solenoid 69 has been de-energised and the solenoid 68 energised so that as soon as the load has substantially been removed from the pin 67, its spring biasing can cause retraction of the pin from the slot 65. When return motion takes place the linkage is free to expand. During return motion, as the third wheels 19 drop relative to the first wheels 17, the road wheels 23 are lowered and engage initially the inclined ramp 24 and the full ballast load is gradually taken up before the road wheels commence rolling across the test pavement 23A.

Computerised control and data analysis is intended, and for this purpose the hub 44 is mounted via four load sensors 65 to brackets 66 at the bottom of the fin 39.

When the solenoid 69 is held in a de-energised condition, the first pin 66 operates under spring biassing to latch the linkage 51 in an intermediate position so that when the trolley has rolled off the curved end portions of the tracks, the road wheels 23 contact neither the road surface 23A nor the base plates 25. Thus the trolley is no longer driven. Furthermore, in the event of electrical power failure, the first pin 66 will engage in slot 65 and thus provide a fail-safe feature.

The preferred embodiment of the invention is designed to be operated with the road wheel at 20 km per hour with the test section being 10 meters long and the road wheel in contact with the test surface in the forward direction only. The road pavement is designed to be a practical test sample and full-size road wheels loaded at up to 2.5 times the legal limit is considered appropriate to provide an effective accelerated loading test for the road pavement.

The preferred embodiment of the invention, by making effective use and transfer of kinetic energy to potential energy, can run on low power inputs and by virtue of each complete cycle of movement taking about 8½ seconds, there is a reasonable opportunity for the pavement to recover after a passage of the wheels representing the passing of a vehicle. Furthermore, by virtue of substantially random, normal distribution of the lateral position of the road wheels, realistic testing of the road surface can be provided in about 100 days, when the machine is run on average of 23 hours per day.

Although various options and alternatives are available it is considered that the preferred embodiment described above represents a highly effective compromise and can permit the fabrication economically of a machine to provide realistic accelerated testing of road surfaces.

We claim:

1. Apparatus for testing a test portion of road pavement extending between first and second positions, the apparatus comprising:
   (a) a support for carrying a test load,
   (b) a hub for rotatably mounting a road wheel on the support,
   (c) mounting means for displaceably mounting and guiding the support for displacement generally between said first and second positions,
   (d) means for moving the support forwardly from the first position to the second position with the road wheel rolling along the test portion, and means for returning the support from the second position to the first position, and characterised by,
   (e) height control means for lifting the hub when the support is in the region of the second position and holding the road wheel out of contact with the road pavement and for maintaining the road wheel out of contact with the test portion during return movement of the support from the second to the first position, the height control means having means for lowering the road wheel onto the test portion during commencement of motion of the support from the first position towards the second position, and
   (f) energy conversion means for decelerating the support and test load as it approaches either the first position or second position and converting the kinetic energy thereof into potential energy and then for accelerating the support and test load in the opposite direction using said potential energy which is converted to kinetic energy.

2. Apparatus as claimed in claim 1, and dimensioned and constructed for carrying test loads of about 40 kN to 100 kN, the hub being adapted to mount a pair of road wheels which are adapted to be driven by said moving means.

3. Apparatus as claimed in claim 1, and wherein the mounting means comprises an elongated track, the support has wheel means arranged to run along said elongated track, and said energy conversion means includes upwardly extending end portions for said elongated track.

4. Apparatus as claimed in claim 1, and wherein said height control means comprises means for absorbing kinetic energy of the decelerating support and test load as they approach the second position and for lifting the hub, and latching means to hold the hub in an elevated position.

5. Apparatus as claimed in claim 3, and wherein said elongated track includes first and second track portions, said wheel means of the support includes first and second wheel means rotatably mounted on an upper structure of the support for engagement respectively on the first and second track portions and having axes on opposite sides of said hub, the hub being mounted on a base element pivotally mounted to the upper structure in the region of the second wheel means, and the height control means comprises:
   (i) third wheel means rotatably mounted on said support at a location generally vertically spaced relative to the first wheel means,
   (ii) a third track portion parallel to and offset laterally relative to said first and second track portions and with end portions which become closer to the first track portion on approaching either end of said track portions, and
   (iii) holding means including:
      (a) a linkage extending upwardly between and connected to the upper structure and the base element at locations on the opposite side of a vertical through the hub compared to the second wheel means, and
      (b) selectively operable fixing means for fixing the linkage in a shortened condition when the support reaches said second position whereby the road wheel is arranged to be held out of contact with the test portion during return motion of the support to the first position, at which location the fixing means releases.

6. Apparatus as claimed in claim 5, and wherein the third wheel means and the linkage have respective cooperating means for holding said third wheel means spaced above the third track portion during return motion of the support from the second position to the first position.

7. Apparatus as claimed in claim 5, and wherein the first, second and third track portions are laterally spaced relative to one another and each comprises a pair of rails, the end portions of the first, second and third track portions being upwardly curved.

8. Apparatus as claimed in claim 7, and wherein the third track portion at the first end position has a smaller radius of curvature than the corresponding parts of the first and second track portions at said first position, and a greater radius of curvature at the second position.

9. Apparatus as claimed in claim 7, wherein the third track portion includes a gap near the end of the test portion at the first position to permit the passage through the gap of the second wheel means, the third wheel means during return motion of the support engages the end portion of the third track portion after passing the gap and continued motion of the support then causes the load to be taken up partially by the third wheel means thereby releasing the load on the linkage.

10. Apparatus as claimed in claim 5, and wherein said fixing means comprises solenoid means arranged to displace a holding pin through a portion of the linkage to hold the linkage in the shortened condition, control means being provided in association with the solenoid means to control its operation.

11. Apparatus as claimed in claim 10, and wherein the solenoid means includes first and second solenoids having respective horizontal pins vertically spaced from one another, and the linkage includes a slot for accommodating the pins of the solenoids, the first solenoid acting as a safety means with a spring for urging the pin into said slot with the first solenoid arranged to be actuated to retract the pin as the trolley reaches the first position, and the second solenoid normally providing the fixing of the linkage and arranged to be energised to displace its pin into said slot against a spring biasing force when the support is at the second position.

12. Apparatus as claimed in claim 5, and including ramp means mounted at the first end position of the test portion for receiving the loaded road wheel as the support starts its motion from the first position towards the second position thereby gradually taking weight off the third wheel means and leading the road wheel onto the test portion.

13. Apparatus as claimed in claim 5, and including elevating means operatable when the hub is stationary for lifting the road wheel off the road pavement.

14. Apparatus as claimed in claim 5 and including motor driven winch means adjacent to the second position for pulling the support towards its end position at which it has acquired potential energy and can then be released to commence operation of the apparatus.

15. Apparatus as claimed in claim 5 and including displacement means for varying laterally the path taken by the road wheel along the test portion, the variation being over a relatively small range of positions.

16. Apparatus as claimed in claim 15, and wherein the displacement means comprises carriages for each end of the mounting means, the carriages being adapted to move on wheels laterally across the road pavement.

17. Apparatus as claimed in claim 1 and wherein the moving means comprises at least one drive motor mounted at the hub and arranged to drive the road wheel continuously, the apparatus further comprising on elongated engagement structure in the mounting means for engagement by the road wheel during motion of the support from the second to the first position.

18. Apparatus for testing road pavement comprising:
 (a) a support having
  (i) an upper frame carrying a test load and first and second pairs of support wheels at respective first and second end regions of the upper frame,
  (ii) a lower structure pivotally mounted on the first end region of the upper frame and mounting via a hub portion road wheel means in a central region, and a pair of guide wheels at the end opposite said pivotal mounting, the guide wheels being generally below said second support wheels,
  (iii) a linkage of variable length interconnecting said upper frame and lower structure in the region of the second end and having selectively operable holding means for holding the linkage in a shortened condition,
 (b) an elongated framework adapted to span over a test portion of said road pavement and having three sets of tracks with respective upwardly curved end portions and for mounting respectively the support wheels and guide wheels, and, in their curved end portions, the tracks for the guide wheels extending progressively closer to the tracks for the second pair of support wheels in the direction towards the adjacent end of the track,
 (c) means for driving the road wheel means, and
 (d) the elongated framework having an elongated plate extending parallel to and above the road pavement for being engaged on its lower surface by the road wheel means when the linkage is held in its shortened condition.

19. Apparatus as claimed in claim 18, and including secondary holding means for said linkage mechanically biassed to a holding position in which the linkage is held partially shortened whereby the road wheel means is held to prevent contact with either the road pavement or the elongated plate.

20. Apparatus as claimed in claim 18, and including means for laterally displacing the framework relative to the road pavement.

* * * * *